United States Patent [19]

Swedo et al.

[11] Patent Number: 5,866,347
[45] Date of Patent: Feb. 2, 1999

[54] METHOD OF IDENTIFYING PERSONS SUSCEPTIBLE TO AUTOIMMUNE NEUROPSYCHIATRIC DISORDERS

[75] Inventors: Susan E. Swedo, McLean, Va.; Henrietta L. Leonard, Providence, R.I.; John B. Zabriskie, New York, N.Y.

[73] Assignee: The United States of America as represented by the Department of Health and Human Services, Washington, D.C.

[21] Appl. No.: 833,653

[22] Filed: Apr. 8, 1997

Related U.S. Application Data

[63] Continuation of Ser. No. 473,033, Jun. 6, 1995, abandoned.

[51] Int. Cl.⁶ ........................ G01N 33/53; G01N 33/564; G01N 33/543; G01N 33/577
[52] U.S. Cl. .................... 435/7.24; 435/7.1; 435/7.21; 435/7.2; 435/7.7; 435/7.9; 435/7.92; 435/960; 435/7.93; 435/7.94; 435/7.95; 435/343; 435/343.1; 436/501; 436/506; 436/514; 436/536; 436/811; 530/388.22; 530/388.7; 530/388.73; 530/388.85; 530/389.6; 530/391.3; 530/391.1
[58] Field of Search .................. 435/7.1, 7.21, 435/7.2, 7.24, 7.7, 7.9, 7.92, 960, 7.93, 7.94, 7.95, 334, 343, 343.1; 436/501, 506, 514, 536, 811; 530/388.22, 388.7, 388.73, 388.85, 389.6, 391.3, 391.1

[56] References Cited

U.S. PATENT DOCUMENTS 4,743,538   5/1988   Zabriskie et al. .

OTHER PUBLICATIONS

Allan Gibofsky, MD, JD; John B. Zabriskie, MD; Rheumatic Fever: New Insights Into An Old Disease, Bulletin on the Rheumatic Diseases, vol. 42, pp. 5–7, Nov. 1993.

Susan E. Swedo, MD; Sydenham's Chorea A Model for Childhood Autoimmune Neuropsychiatric Disorders: JAMA, Dec. 14, 1994 –vol. 272, No. 22, pp. 1788–1791.

Harvey S. Singer; Neurobiological Issues in Tourette Syndrome; Brain and Development vol. 16: 353–364, 1994.

Susan E. Swedo, MD et al.; Sydenham's Chorea: Physical and Psychological Symptoms of St Vitus Dance; Pediatrics vol. 91 No. 4; Apr. 1993, pp. 706–713.

Susan E. Swedo, MD, Henrietta L. Leonard, MD, and Judith L. Rapoport, MD; Childhood–Onset Obsessive Compulsive Disorder; Psychiatric Clinic of North America, vol. 15 No. 4; Dec. 1992, pp. 767–775.

G.V.H. Herdy, J.B. Zabriskie, F. Chapman, A. Khanna and S. Swedo; A Rapid Test For the Detection of A B–Cell Marker (D8/17) In Rheumatic Fever Patients, Brazil. J. Med. Biol. Re., 25:789–794, 1992.

Allan Gibofsky, Ashwani Khanna, Elsa Suh, and John B. Zabriskie; The Genetics of Rheumatic Fever: Relationship to Streptococcal Infection and Autoimmune Disease. J. Rheumatol., 18: 1–5, 1991.

A. Khanna, D. Buskirk, R. Williams, A. Gibofsky, M. Crow, A. Menon, M. Fotino, H. Reid, T. Poon–King, P. Rubinstein and J. Zabriskie; Presence of a non–HLA B Cell Antigen In Rheumatic Fever patients and their families as defined by a monoclonal antibody. J. Clin. Invest., 83: 1710–1716, 1989.

A.J. Allen, M.D., Ph.D., et al.; Case Study: A New Infectious–Triggered, Autoimmune Subtype of Pediatric OCD and Tourette's Syndrome; J. Am. Acad. Child Adolesc. Psychiatry, vol. 34, No. 3, Mar. 1995, pp. 307–311.

Feldman, et al.; J. of Ped., 123:84–86, 1993.

Seaver, Gen. Eng. News, 14:10,21, 1994.

*Primary Examiner*—Ronald B. Schwadron
*Attorney, Agent, or Firm*—Knobbe, Martens, Olson & Bear, LLP

[57] ABSTRACT

A method of identifying individuals who have, or who are at risk of developing, autoimmune neuropsychiatric disorders is disclosed. The invented method relies on detection of the B lymphocyte antigen, D8/17. The invented method can conveniently be carried out as a simple blood test.

16 Claims, No Drawings

METHOD OF IDENTIFYING PERSONS SUSCEPTIBLE TO AUTOIMMUNE NEUROPSYCHIATRIC DISORDERS

This application is a continuation of U.S. application Ser. No. 08/473,033, filed Jun. 6, 1995, now abandoned.

FIELD OF THE INVENTION

The present invention relates to a method of identifying persons with, or at risk of developing, autoimmune neuropsychiatric disorders. More specifically, the invention relates to the new use of an antibody-based test for detecting the D8/17 antigen on B lymphocytes of affected and at risk individuals.

BACKGROUND OF THE INVENTION

Obsessive Compulsive Disorder (OCD) is characterized by recurrent thoughts (obsessions) and/or repetitive rituals (compulsions) that are distressful and/or interfere in one's life (American Psychiatric Association, *Diagnostic and Statistical Manual of Mental Disorders,* 4th ed. (DSM-IV), Washington, D.C.: American Psychiatric Association (1994)). The obsessive thoughts may include worries about the safety of oneself or family members, past actions, or fears of contamination. The rituals are often performed in response to an obsession and include repetitive washing, checking, counting, repeating, arranging, or hoarding. Childhood onset OCD has been reviewed by Swedo, et al., in *Psychiatric Clinics of North America* 15: 767 (1992). There is no known biologic marker or genetic marker, despite some evidence that childhood onset OCD may be biologically based. Lenane, et al., in *J. of the American Academy of Child and Adolescent Psychiatry* 29: 407 (1990), reported that parents of a patient group of children with OCD had an increased family rate of OCD, suggesting a genetic vulnerability for some.

Tourette's Syndrome (TS) or Tourette's Disorder is a childhood onset disorder characterized by involuntary motor and vocal tics of more than one year's duration which typically change anatomic location, number, frequency, complexity, and severity over time (DSM IV). Chronic motor tic, chronic vocal tic, and transient tic disorders are characterized by the same involuntary motor or vocal tics, but are not of sufficient duration to meet diagnostic criteria for TS (DSM-IV). Tic disorders and TS have been reviewed by Singer, et al., in *Brain and Development* 16: 353 (1994). There may be an association between OCD and tic disorders; as children with OCD have an increased rate of a comorbid (coexisting) tic disorder (Leonard, et al., *Am. J. of Psychiatry* 149: 1244 (1992)), and individuals with TS have an increased rate of obsessive compulsive symptoms (Pauls et al., *Arch. Gen. Psychiatry* 43: 1180 (1986)). Additionally, individuals with TS have an increased rate of familial OCD and tic disorders (Pauls et al., 1986).

Sydenham's Chorea (SC), first described in the late 1600s as "St. Vitus dance," is a type of rheumatic fever (RF) and is characterized by muscular weakness and chorea (reviewed by Swedo et al., in *Pediatrics* 91: 706 (1993)). The muscle weakness and adventitious movements may lead to a clumsy gait, slurred speech, and the inability to hold a grip. Historically, this neurological disorder has been described to have accompanying psychological symptoms in some patients, including emotional lability, irritability, and obsessive compulsive symptoms. Recently, some children with SC who had accompanying OCD, Attention Deficit Hyperactivity Disorder, emotional lability, and irritability have been described (Swedo et al., 1993).

Sydenham's chorea- is a variant of RF that is thought to result from an autoimmune process mediated by antineuronal antibodies. The self-reactive antibodies appear to arise in response to group A β-hemolytic streptococci (GABHS) infections and then cross-react with antigens on neuronal cells within the basal ganglia and other brain regions (Husby et al., *J. Exp. Med.* 144: 1094 (1976)). The choreic symptoms could be caused either directly by antineuronal antibodies, or indirectly by altering immune responsivity or permeability of the blood brain barrier. Significantly, each of these mechanisms is reported to be under genetic control (*Int. Rev. Cytol.* 127: 57 (1991)).

SUMMARY OF THE INVENTION

One aspect of the invention provides a method of determining whether a human subject has susceptibility to an infection triggered autoimmune neuropsychiatric disorder. The invented method includes the steps of first obtaining a sample containing B lymphocytes from the subject, and then testing the B lymphocytes for the presence of alloantigen D8/17. The presence of the D8/17 antigen on the B lymphocytes indicates that the subject has a susceptibility to autoimmune neuropsychiatric disorders. In one embodiment, the sample containing B lymphocytes is a blood sample that is collected from a finger prick or by venous puncture.

In a preferred embodiment, an immunohistochemistry assay is employed to test the B lymphocytes for the presence of alloantigen D8/17. This immunohistochemistry assay can employ an antibody reagent that may be a monoclonal antibody. The monoclonal antibody can be the monoclonal antibody that is produced by the HB8783 hybridoma cell line. A visible color change may be used to indicate the presence of this antibody reagent in the immunohistochemistry assay. Further, the assay can be performed such that either microscopy or flow cytometry is employed as a detection system. In still another embodiment of the immunohistochemistry assay, an ELISA assay is used to test the subject's B lymphocytes for the presence of the D8/17 alloantigen.

Other preferred embodiments of the invented method regard the neuropsychiatric disorders for which susceptibility is being tested. In one preferred embodiment, the invented method is used for determining if the subject has susceptibility to an infection triggered autoimmune childhood obsessive compulsive disorder. In another preferred embodiment, the invented method is used for determining if the subject has susceptibility to an infection triggered autoimmune childhood onset tic disorder. In another preferred embodiment, the invented method is used for determining if the subject has susceptibility to infection triggered autoimmune childhood onset Tourette's syndrome. In another preferred embodiment, the invented method is used for determining if the subject has susceptibility to infection triggered autoimmune Attention Deficit Hyperactivity Disorder. In yet another preferred embodiment, the invented method is used when the subject has no prior history of a neuropsychiatric disorder.

DETAILED DESCRIPTION OF THE INVENTION

We have discovered that an antibody-based test for detecting the presence of the D8117 B lymphocyte alloantigen can be used to identify pediatric patients with a clinical picture of abrupt onset or exacerbation of neuropsychiatric symptoms following an infectious illness, specifically GABHS, and others who are at-risk of developing such disorders. Identification of this at-risk population is important because the autoimmune response that exacerbates these patients' neuropsychiatric disorders is controllable. For example, early treatment of streptococcal infections with antibiotics can limit the body's need to mount a vigorous immune response. For those having the genetic vulnerability to develop antineuronal antibodies, such intervention might block development of the symptoms or exacerbation. This effectively blunts increases in neuropsychiatric symptoms, such as obsessions, compulsions, tics, inattentiveness or others, brought on by the production of an anti-strep humoral immune response. Under a contemplated regimen of preventive care, periodic throat cultures for asymptomatic GABHS infections are carried out with appropriate treatment of individuals having positive cultures. Further, individuals who are at risk of autoimmune neuropsychiatric symptoms can be enrolled in a program of antibiotic prophylaxis in order to prevent the possible onset of a strep infection that would exacerbate the patient's condition.

We have recently reported (Allen et al., *J. Am. Acad. Child Adolesc. Psychiatry* 34: 307 (1995)) on a subgroup of pediatric patients with OCD and/or tic disorders having cycles of clinically significant symptoms distinguished by a sudden, dramatic onset followed by a slow waning over a period of months. This pattern was somewhat similar to the course of symptoms in Sydenham's chorea (Swedo, S.E., *JAMA* 272: 1788 (1994)). In addition to the choreic movements, some Sydenham's patients may exhibit tic-like movements. Indeed, the phenomenon of tic exacerbation has recently been addressed by Kiessling, et al., (*Pediatrics* 92: 39 (1993)) in a report on patients having increased tics after a community outbreak of streptococcal pharyngitis.

These observations led us to investigate whether streptococcal infections, "strep throats" and other infections caused by GABHS, in pediatric patients could trigger the sudden onset or episodic worsening of OCD and/or tic disorders, including TS, via an autoimmune process analogous to Sydenham's chorea (Swedo S.E., *JAMA* 272: 1788 (1994); Swedo et al., *Pediatrics* 93: 323 (1994)).

Herein we disclose that immunomodulatory treatments can improve symptoms for OCD and tic disorder/TS patients having severe illness that is exacerbated by an autoimmune response. The essential features of these cases are summarized by the phrase: pediatric, infection-triggered, autoimmune neuropsychiatric disorders (PITANDs). As disclosed below, some of these cases may be triggered by viruses rather than GABHS. A set of subjective criteria for identifying PITAND cases is also disclosed.

As the result of our work with children in the Child Psychiatry Branch, National Institute of Mental Health (NIMH) clinic for OCD, tic disorders (including TS) and attention-deficit hyperactivity disorder (ADHD), we noted that some children developed the first onset of, or the acute exacerbation of, neuropsychiatric symptoms following infectious illness. Some of the children developed abrupt onset of OCD, tics, and accompanying behavioral and affective disturbances following GABHS infections. Although each patient had a diagnosis of OCD and/or tic disorder, some additionally had ADHD, mood disorders, and anxiety disorders. Some of our clinical observations of children with neuropsychiatric disorders, specifically OCD, tic disorders, and ADHD, who had an acute onset and/or dramatic exacerbation following infectious illness, have recently been published in *J. Am. Acad. Child Adolesc. Psychiatry* 34: 307 (1995).

In the following Example, a group of children with OCD, tic disorders, ADHD, and other neuropsychiatric disorders, who appeared to have abrupt onset or dramatic onset of neuropsychiatric symptoms following infectious illness, including GABHS, were sought via advertisements through professional medical organizations. We hypothesized that an autoimmune response in children with OCD, tic disorders, ADHD, and other neuropsychiatric disorders, who developed acute onset or exacerbation of their infections subsequent to GABHS or other infections, might underlie the pathophysiology of the children's neuropsychiatric disorders. Significantly, the population of children recruited for this study did not have RF or SC.

Example 1 presents four pediatric cases who were treated in an open. National Institute of Mental Health (NIMH) trial. Significantly, these cases represented a subclass of children having OCD and/or tic disorders whose neuropsychiatric symptoms were exacerbated following infection.

Example 1

A New Infection-Triggered, Autoimmune Subtype of Pediatric OCD and Tourette's Syndrome: Four Case Studies Case 1

B. J. was a 14year-old with a 1.5-year history of OCD and mild tics which had been stable for several months while he was taking a combination of clomipramine and fluoxetine. Then, during a summer soccer camp, his OCD symptoms suddenly worsened dramatically. On his return home a throat culture was done. The culture was positive and GABHS pharyngitis was diagnosed, although B. J.'s last sore throat had resolved a month earlier. Two weeks later he came to the NIMH for evaluation. His obsessions included a fear for his own and his father's safety, a need for symmetry and perfectionistic concerns. His predominate compulsions were checking behaviors and exercises (e.g., fingertip pushups) that had to be performed perfectly or repeated until he was unable to continue. At that time, more than 90% of his waking hours were occupied by obsessions and compulsions. Neurological examination revealed motoric hyperactivity and mild choreiform movements.

Because of the severity of B. J.'s OCD, his suspicious movements, and his sudden worsening during a streptococcal infection, he was treated with a series of six plasma exchanges over a period of two weeks. During this time there was a marked decline in his OCD symptoms (Table 1). Subjectively, the patient and his family reported he was "80% better." A magnetic resonance imaging scan done after four plasma exchanges showed a 25% decrease in the size of the head of the caudate compared to a scan done before treatment (Swedo et al., *Pediatrics* 93: 323 (1994)). After plasmapheresis he began a regimen of penicillin as prophylaxis against GABHS infections. He continued to do well at follow-up several months later.

Case 2

T. J. was a 10-year-old who had no history of psychiatric or neurological problems. The weekend after several family members had the "flu," he experienced a sudden onset of severe obsessions about viruses and chemicals. He additionally began compulsive hand-washing. After a month of continuous illness, psychiatric treatment was sought and he started sertraline therapy, with only partial symptom relief of his OCD after two months. He was then evaluated at the NIMH (three months after the onset of his illness). At that time his forearms and hands were chapped and red, and contamination fears prevented him from fully opening his mouth so that he was unable to eat in the hospital or have a throat culture.

Because of the abrupt onset of his symptoms and their severity, T. J. was treated with six plasma exchanges over a period of two weeks. Penicillin prophylaxis was not prescribed because his episode of OCD appeared to have been virally triggered. His symptoms declined noticeably during plasmapheresis—after the fourth exchange he could eat at the hospital and permitted a throat culture. His symptoms were so improved one month after plasmapheresis that his sertraline dosage was being tapered, with only subclinical obsessions and compulsions remaining (Table 1). He was reported to be doing well several months later.

Case 3

In 1987, when S. J. was seven years old, painful ulcers developed on his mouth and lips, and he was noted to have a positive antinuclear antibody titer with speckled pattern. Shortly after this, he had the first of many GABHS infections, which continued until 1989 when he had a tonsillectomy. After the surgery he began to experience motor tics (craning of his neck, eye-blinking, shoulder-shrugging) and vocal tics ("clicking" sounds), which were eventually diagnosed as TS. His tics declined after he began to take a low dose of fluphenazine and were stable for approximately 18 months. Shortly after a bout of the "flu," his tics escalated dramatically. Of particular concern were new, violet tics of his head and neck that were so extreme that S. J. had physical discomfort. Now 13 years old, he was referred to NIMH for evaluation. He was found to have an antinuclear antibody titer of 1:320 (speckled pattern), and subsequently a transient rash developed. A rheumatologist concluded that he did not have lupus, however.

Six months after his viral illness, S. J. was treated with immunosuppressive doses of prednisone. A clinically significant improvements in his tics were evident two weeks later (Table 1), although residual movement remained. His tics again worsened suddenly a few weeks later, after a viral respiratory infection and an allergic reaction to an influenza immunization. A retrial of prednisone at that time was unsuccessful.

Case 4

J. J. was a 13-year-old with a long history of asthma, hyperactivity, TS and OCD. He had previously been enrolled in several protocols at the National Institutes of Health (NIH) for these illnesses. His neuropsychiatric symptoms were believed to be episodic but had been relatively well controlled for about six months while he was taking a combination of methylphenidate and clomipramine. After a documented case of GABHS pharyngitis, he experienced rapid, severe worsening of both his TS and OCD. This occurred during a family trip to Thailand and Arizona, during which the family had to alter their travel plans because of J. J.'s obsessive fears that the plane would crash. J. J. also had severe vocal tics (spitting and nearly continuous screaming) during the trans-Pacific flights, and he was unable to finish any reading material because he felt the need to reread every sentence many times.

Approximately 2.5 months after his infection and a month after his symptoms increased, he was treated with intravenous immunoglobulin (1 mg/kg per day for two days). His parents reported that his tics began to improve within a week of the intravenous immunoglobulin treatment. At one month follow-up Table 1), there was a clinically significant improvement in his tics, but his OCD was essentially unchanged. His parents reported that J. J. was doing well several months later, at which time he entered a NIH protocol comparing penicillin with placebo as prophylaxis against neuropsychiatric episodes triggered by GABHS infections.

Table 1 summarizes the relevant findings, treatments and results from the four case studies presented above.

TABLE 1

Demographic, Clinical and Treatment Data

| | Case 1 (B.J.) | Case 2 (T.J.) | Case 3 (S.J.) | Case 4 (J.J.) |
|---|---|---|---|---|
| Sex, age (years) | Male, 14 | Male, 10 | Male, 13 | Male, 13 |
| Diagnosis (including predominate obsessions and compulsions) | Mild motor and vocal tics, OCD (exercise, need for perfection) | OCD (contamination) | TS | ADHD, TS, OCD (contamination, rereading, need for perfection) |
| Prodromal symptoms or prior episodes | Yes | No | Yes | Yes |
| Suspected infectious trigger for treatment episode | GABHS pharyngitis (positive culture) | Viral, possibly influenza | Viral, possibly influenza | GABHS pharyngitis (positive culture) |
| Duration of episode before treatment | 2 weeks | 3 months | 5 months | 1 month |
| Laboratory results before treatment | ASO = 340 Anti-DNAse B = 1:340 ANA negative | ASO, ANA negative | ASO = 240 ANA positive, 1:320, speckled | ASO, ANA negative |
| Pretreatment ratings[a] | C-YBOCS = 40 (maximum possible score) | C-YBOCS = 25 | Ex MTR = 13 Ex VTR = 2 Hx MTR = 18 Hx VTR = 5 | C-YBOCS = 28 Ex MTR = 9 Ex VTR = 12 Hx MTR = 16 Hx VTR = 19 |
| Treatment | Plasmapheresis | Plasmapheresis | Prednisone | IVIG |

TABLE 1-continued

Demographic, Clinical and Treatment Data

|  | Case 1 (B.J.) | Case 2 (T.J.) | Case 3 (S.J.) | Case 4 (J.J.) |
| --- | --- | --- | --- | --- |
| Posttreatment ratings[b] (% change from pretreatment) | C-YBOCS = 19.5 (−51%) | C-YBOCS = 10 (−60%) | Ex MTR = 8 (−38%) Ex VTR = 2 (0%) Hx MTR = 10 (−44%) Hx VTR = 0 (−100%) | C-YBOCS = 26 (−7%) Ex MTR = 4 (−56%) Ex VTR = 4 (−67%) Hx MTR = 6 (−62%) Hx VTR = 12 (−37%) |

Note:
OCD = Obsessive-compulsive disorder; TS = Tourette's syndrome; ADHD = attention-deficit hyperactivity disorder; GABHS = Group A β-hemolytic streptococci; ASO = anti-streptolysin O; Anti-DNAse B = anti-streptococcal DNAse B; ANA = antinuclear antibodies; C-YBOCS = Children's Yale-Brown Obsessive Compulsive Scale (Goodman et al., Psychiatr. Clin. North Am. 15:861 (1992)) (a score of 20 reflects OCD symptoms of moderate severity; scores range from 0 to 40); Ex MTR = Examiner's motor tic ratings on the Shapiro tic rating scale (Shapiro et al., Gilles de la Tourette Syndrome New York: Raven Press (1978)) (a score of 12 reflects tics of moderate severity; scores range from 0 to 20); Ex VTR = examiner's vocal tic ratings on the Shapiro tic rating scale (Shapiro et al., Gilles de la Tourette Syndrome New York: Raven Press (1978)); Hx MTR = historical (from parent/child) motor tic ratings on the Shapiro tic rating scale (Shapiro tic ratings on the Shapiro tic rating scale (Shapiro et al., 1978): IVIG = intravenous immunoglobulin.
[a]All ratings shown are the means from two physicians with training in mental health research.
[b]Posttreatment ratings are within a month of completing treatment.

The following subjective criteria can be used to accurately identify PITAND patients:
1. Pediatric onset: symptoms of the disorder first become evident between three years of age and the beginning of puberty.
2. At some time in his or her life, the patient must have met diagnostic criteria for OCD and/or a tic disorder.
3. The onset of clinically significant symptoms must be sudden (with or without a subclinical prodrome), and/or there must be a pattern of sudden, recurrent, clinically significant symptoms exacerbations and remissions. Onset of a specific episode typically can be assigned to a particular day or week, at which time symptoms seemed to "explode" in severity.
4. Increased symptoms should not occur exclusively during stress or illness, should be pervasive, should be of sufficient severity to suggest the need for treatment modifications, and (if untreated) should last at least four weeks before improvement is noted.
5. During OCD and/or tic exacerbations, the majority of patients will have an abnormal neurological examination, frequently with adventitious movements (e.g., mild chorea).
6. There must be evidence of an antecedent or concomitant infection. Such evidence might include a positive throat culture, positive streptococcal serological findings (e.g., anti-streptolysin O or anti-streptococcal DNAse B), or a history of illness (e.g., pharyngitis, sinusitis, or flu-like symptoms).
7. Patients may or may not continue to have clinically significant symptoms between episodes of their OCD and/or tic disorder.

Given our identification of a population of children having a disorder with a unique symptomology, we investigated a comparison between pediatric OCD/tic disorders/TS patients whose symptoms had onset or exacerbation after GABHS infection and SC patients. These clinical observations of SC, OCD, and tic disorders led us to test whether a D8/17 immunoassay could be used to identify individuals afflicted with, or at risk of developing, autoimmune neuropsychiatric disorders including OCD and/or tic disorders. A test for the D8/17 B lymphocyte alloantigen is the subject of U.S. Pat. No. 4,743,538. The monoclonal antibody, D8/17, appears to identify a cell-surface marker which shows increased expression on B cells of rheumatic fever patients (Khanna et al., J. Clin. Invest. 83: 1710 (1989)). The hybridoma producing monoclonal antibody was deposited with the American Type Culture Collection, 12301 Parklawn Drive, Rockville, Md. 20852 on Apr. 16, 1985 under accession number HB8783. This deposit was converted to a deposit under the Budapest Treaty on Jan. 16, 1997. This B cell alloantigen marker is present ("positive") in 90–100% of patients with RF (Gibofsky et al., J. Rheumatol (supp. 130) 18: 1–5 (1991)). The D8/17 antigen is unique to individuals who have had (or had risk for) RF illness and is considered to be a genetic marker for individuals who are genetically vulnerable to develop RF. An individual who had more than 12% (mean plus one standard deviation above normal values) of their B (DR) cells exhibiting the D8/17 marker was labeled "positive". An individual with less than 12% of their B (DR) cells exhibiting this marker was considered "negative." The % positive D8/17 cells was calculated as [(D8/17 positive cells)/(DR cells)]×100 (Gibofsky et al., 1991).

Ninety to 95% of healthy persons have less then 12% of their B cells positive for the D8/17 marker, and therefore are considered negative for this marker (Gibofsky et al., 1991). Rodrigues, et al. (Pathogenic Streptococci Present and Future, Lancer Publication, St. Petersburg, Russia (1994)) reported that, of 1,854 healthy school-aged children in Mexico who were randomly tested for the marker, only 5% were found to be D8/17 positive. A small proportion of normals (5–10%) will be D8/17 positive, but among patients with rheumatic fever, 95% will be positive for the marker. This indicated an abnormal expansion of the population of D8/17 positive B cells and increased susceptibility to RF (Gibofsky et al., 1991).

Importantly, the presence of streptococcal infection per se was not associated with an increased number of B cells staining positive for D8/17 antigen in individuals with streptococcal infections but without rheumatic fever. Specifically, patients with well documented poststreptococcal glomerulonephritis and others with documented GABHS tonsillitis did not have positive results for the D8/17 marker (Kemeny et al., Clin. Immunology and Immunopathology 72: 35 1994; Khanna et al., 1989).

We discovered that a blood test that identified RF susceptibility also identified individuals susceptible to autoimmune OCD/tic disorders. In view of the fact that the children participating in this study did not have RF or SC, one could not have predicted in advance that these children would be D8/17 positive.

With respect to the immunohistochemical methods useful in identifying D8/17 positive individuals, variations on the techniques disclosed below will be apparent to those having ordinary skill in the art. For instance, while light microscopy was employed to detect positively staining cells in the following Example, we anticipate that other techniques such as flow cytometry and ELISA procedures could be adapted for use with the present invention. Additionally, we have found that blood samples obtained either by venous puncture or finger prick methods can be used with the following procedure.

Example 2 describes the method used to detect the D8/17 positive B cell antigen in blood samples from children whose neuropsychiatric symptoms were exacerbated following infectious illness.

Example 2

Immunodetection of the D8/17 Antigen in Blood Samples

Immunohistochemical analysis of blood samples was performed according to standard laboratory procedures. A description of the monoclonal antibody used for detecting the D8/17 B cell antigen can be found in U.S. Pat. No. 4,743,538, the disclosure of which is hereby incorporated by reference.

A 300 $\mu$l sample of citrated blood was transferred to a polystyrene tube, such as a FALCON 2058. A 100 $\mu$l volume of the D8/17 antibody produced by hybridoma HB8783 was added to the blood sample and then incubated for 1 hour at 4° C. The mixture was washed once using 2 mls of PBS-BSA buffer and centrifuged at 1500 rpm for 5 minutes to gently pellet the cells. A 1 liter preparation of the PBS-BSA buffer contained 8 g of NaCl, 400 mg of KCl, 1.15 g of $Na_2HPO_4$, 10 g of bovine serum albumin, 1 g sodium azide, and was adjusted to a pH of 7.4. After this first wash step, 20 $\mu$l of fluorescein isothiocyanate (FITC) conjugated goat anti-mouse IgM was added and incubated for 45 minutes at 4° C. The mixture was then washed as before to remove unbound antibodies. Next, 15 $\mu$l of phycoerythrin conjugated anti-human HLA-DR antibody was added and incubated for 20 minutes at 4° C. The mixture was again washed as before. A 3 ml volume of lysis buffer was added and mixed thoroughly. The mixture was incubated for 3–4 minutes before a 3 minute centrifugation at 1000 rpm. Lysis buffer was prepared by combining 0.9 g $NH_4Cl$, 0.19 g $KHCO_3$, 0.05 ml 10% EDTA and diluting to a final volume of 100 ml using distilled water. The lysate was washed twice as before, and then counted for stained cells by standard laboratory procedures as would be familiar to one having ordinary skill in the art.

Results of this immunohistochemical analysis from subjects at the NIMH are shown below in Table 2. Of the SC patients, 89% were positive for the B cell D8/17 marker. This result was expected based on the fact that U.S. Pat. No. 4,743,538 indicates the D8/17 antigen is a marker for the risk of developing RF, and that SC is a variant of RF. Also expected, only 10% of the normal controls were positive for the D8/17 antigen. This is consistent with previous estimates that only 5–10% of the population may express this marker. As hypothesized, 93% of the children with GABHS mediated (nonRF, nonSC) neuropsychiatric symptoms were D8/17 positive. Diagnoses of these patients included OCD and/or a tic disorder with some additionally having ADHD, an anxiety disorder, a mood disorder, or some behavior disorder. This was significantly increased over the value that would be expected in a random population. Nothing in the clinical presentation of the symptoms suggested that these children should have had such a high rate of the marker; thus, this is a novel clinical application of the technique.

TABLE 2

Frequency of Individuals Positive for Expression of B cell D8/17 Marker in Various Patient Populations

| Patient Population | % of Population D8/17 Positive |
|---|---|
| Normal Control | 10 |
| Sydenham's Chorea | 89 |
| GABHS-mediated (non-RF; non-SC) Neuropsychiatric Symptoms | 93 |

We have also obtained evidence that the D8/17 marker has predictive value in identifying individuals who, while unaffected at the time of testing, may go on to develop autoimmune neuropsychiatric disorders in the future. More specifically, some of the unaffected siblings of the D8/17 positive pediatric patients were tested for the presence of the D8/17 marker. Two siblings of separate patients were found to be D8/17 positive and subsequently developed OCD and/or tics. In addition, one proband with OCD had two male siblings, one with TS (already diagnosed) who was D8/17 positive and one who was D8/17 negative and evidenced no neuropsychiatric symptoms.

We have demonstrated that a positive test for the D8/17 antigen can identify individuals who have OCD, tic disorders/TS, and/or other autoimmune neuropsychiatric disorders. Further, a positive test for the D8/17 antigen has been shown to identify individuals at genetic risk for these disorders. Thus, the D8/17 test has diagnostic and prognostic implications and may be useful in the prevention of these neuropsychiatric disorders, as well as identifying patients for whom novel therapies may be useful. With estimates that 1% of all children and adolescents have OCD, and that 5–10% have a tic disorder, this technique will have application in a large number of individuals.

What is claimed is:

1. A method of determining whether a human subject has susceptibility to an autoimmune neuropsychiatric disorder other than Sydenham's chorea, comprising the steps of:
   (a) obtaining a sample containing B lymphocytes from the subject; and
   (b) testing the B lymphocytes for the presence of the antigen recognized by the monoclonal antibody produced by the ATCC HB8783 cell line, wherein the presence of said antigen indicates that the subject has a susceptibility to said autoimmune neuropsychiatric disorder.

2. The method of claim 1, wherein said sample containing B lymphocytes is a blood sample.

3. The method of claim 2, wherein said blood sample is collected from a finger prick or venous puncture.

4. The method of claim 1, wherein the testing step comprises an immunohistochemistry assay.

5. The method of claim 1, wherein the testing step comprises contacting said B lymphocytes with a monoclonal antibody.

6. The method of claim 5, wherein the monoclonal antibody is produced by the ATCC HB8783 hybridoma cell line.

7. The method of claim 4, wherein the immunohistochemistry assay comprises microscopy.

8. The method of claim 4, wherein the immunohistochemistry assay comprises flow cytometry.

9. The method of claim 4, wherein the immunohistochemistry assay is an ELISA assay.

10. The method of claim 1, wherein said disorder is childhood obsessive compulsive disorder.

11. The method of claim 1, wherein said disorder is a childhood onset tic disorder.

12. The method of claim 1, wherein said disorder is childhood onset Tourette's syndrome.

13. The method of claim 1, wherein said disorder is Attention Deficit Hyperactivity disorder associated with a GABHS-triggered autoimmune neuropsychiatric disorder.

14. The method of claim 1, wherein the subject has no prior history of a neuropsychiatric disorder.

15. The method of claim 1, wherein the neuropsychiatric disorder is a group A $\beta$-hemolytic streptococci (GABHS)-triggered autoimmune neuropsychiatric disorder.

16. The method of claim 1, wherein the autoimmune neuropsychiatric disorder is a childhood-onset neuropsychiatric disorder.

* * * * *

UNITED STATES PATENT AND TRADEMARK OFFICE
CERTIFICATE OF CORRECTION

PATENT NO. : 5,866,347
DATED : February 2, 1999
INVENTOR(S) : Swedo et al.

It is certified that error appears in the above-identified patent and that said Letters Patent is hereby corrected as shown below:

On the title page item [73],

The correct name and address of the assignee is:

The United States of America as Represented by the Department of Health and Human Services, Washington, DC, and Rockefeller University, New York, NY.

Signed and Sealed this

Twenty-eighth Day of March, 2000

Attest:

Q. TODD DICKINSON

*Attesting Officer*

*Commissioner of Patents and Trademarks*